(12) United States Patent
Kalindjian et al.

(10) Patent No.: US 7,034,048 B2
(45) Date of Patent: Apr. 25, 2006

(54) GASTRIN AND CHOLECYSTOKININ RECEPTOR LIGANDS (III)

(75) Inventors: Sarkis Barret Kalindjian, London (GB); Ildiko Maria Buck, London (GB); Caroline Minli Rachel Low, London (GB); Matthew John Tozer, London (GB)

(73) Assignee: James Black Foundation Limited, London (GB)

( * ) Notice: Subject to any disclaimer, the term of this patent is extended or adjusted under 35 U.S.C. 154(b) by 0 days.

(21) Appl. No.: 10/275,613

(22) PCT Filed: May 4, 2001

(86) PCT No.: PCT/GB01/01982

§ 371 (c)(1),
(2), (4) Date: Apr. 10, 2003

(87) PCT Pub. No.: WO01/85724

PCT Pub. Date: Nov. 15, 2001

(65) Prior Publication Data

US 2003/0191116 A1   Oct. 9, 2003

(30) Foreign Application Priority Data

May 8, 2000    (GB)   .................................. 0011092.4

(51) Int. Cl.
  A61K 31/4164   (2006.01)
  A61K 31/404    (2006.01)
  C07D 403/04    (2006.01)
(52) U.S. Cl. .................... 514/397; 548/217; 548/300.1; 548/302.7; 548/306.1; 548/469; 548/470; 514/387
(58) Field of Classification Search ............. 548/300.1, 548/302.7, 306.1, 217, 469, 470; 514/387, 514/397
See application file for complete search history.

(56) References Cited

U.S. PATENT DOCUMENTS 5,719,143 A     2/1998  Badorc et al.
6,150,379 A  *  11/2000  Fatheree et al. ............ 514/338

FOREIGN PATENT DOCUMENTS

GB   2 290 539         1/1996
WO   WO 93 12817 A   7/1993

OTHER PUBLICATIONS

Susan E. Gibson et al., Incorporation of Conformationally Constrained Phenylalanine Derivatives TIC, SIC, HIC and NIC Into A Cholecystokinin-B/Gastrin Receptor Antagonist. Patent Abstracts of Japan, JP 06 092961; Shikoku Chemical Corporation, Apr. 5, 1994.

E. Lindstrom et al., Pharmacological Analysis of CCK2 Receptor Antagonists Using Isolated Rat Stomach ECL Cells; British Journal of Pharmacology, vol. 127, 1999, pp. 530-536, XP001000286, p. 531, col. 1, paragraph 2.

* cited by examiner

Primary Examiner—Golam M. M. Shameem
(74) Attorney, Agent, or Firm—Heller Ehrman LLP

(57) ABSTRACT

Compounds of formula (I) and their pharmaceutically acceptable salts are ligands at gastrin and/or cholecystokinin receptors. X and Y are independently =N—, —N($R^5$)—($R^5$ being selected from H, Me, Et, Pr, Bn, OH and —$CH_2COOR^6$, wherein $R^6$ represents H, Me, Et, Pr or Bn), =CH—, —O— or —S—; n is from 1 to 4; A is an optionally substituted 5- or 6-membered carbocyclic ring wherein (a) 1 or 2 C atoms may optionally be replaced by N, O and/or S atoms, (b) A is fused with the aromatic group in formula (I) to form a fused bicycle, and (c) the ring containing X and Y is linked to a C atom of A; $R^1$ is H or $C_1$ to $C_{15}$ hydrocarbyl wherein up to three C atoms may optionally be replaced by N, O and/or S atoms and up to three H atoms may optionally be replaced by halogen atoms; $R^2$ is selected from H, Me, Et, Pr and OH, each $R^2$ being independently selected from H, Me, Et, Pr and OH when n is greater than 1; $R^3$ (when n is 1) is selected from H, Me, Et and Pr; or (when n is greater than 1) each $R^3$ is independently selected from H, Me, Et and Pr, or two $R^3$ groups on neighbouring carbon atoms are linked to form a $C_3$ to $C_6$ carbocylic ring, or two $R^3$ groups are absent from neighbouring carbon atoms which are linked by a double bond; or $R^2$ and $R^3$ on the same carbon atom together represent an =O group; $R^4$ is $C_1$ to $C_{15}$ hydrocarbyl wherein up to two C atoms may optionally be replaced by N, O and/or S atoms and up to three H atoms may optionally be replaced by halogen atoms; V is —CO—NH—$SO_2$—Ph, —$SO_2$—NH—CO—PH, —$CH_2OH$, or a group of the formula —$R^7U$, (wherein U is —COOH, tetrazolyl, —CONHOH or —$SO_3H$; and $R^7$ is a bond; $C_1$ to $C_6$ hydrocarbylene optionally substituted by hydroxy, amino or acetamido; —O—($C_1$ to $C_3$ alkylene)—; —$SO_2NR^8$—$CHR^9$—; —CO—$NR^8$—$CHR^9$—, $R^8$ and $R^9$ being independently selected from H and methyl; or —NH—(CO)$_c$—$CH_2$, c being 0 or 1); or a pharmaceutically acceptable salt thereof. Compositions comprising a compound a formula (I) are also described

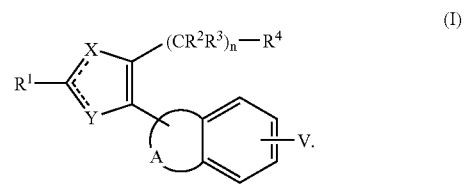

22 Claims, No Drawings

GASTRIN AND CHOLECYSTOKININ RECEPTOR LIGANDS (III)

This application is the national phase under 35 U.S.C. § 371 of PCT International Application No. PCT/GB01/01982 which has an International filing date of May 4, 2001, the disclosure of which is incorporated herein by reference in its entirety.

This invention relates to gastrin and cholecystokinin (CCK) receptor ligands. (The receptor previously known as the $CCK_B$/gastrin receptor is now termed the $CCK_2$ receptor). The invention also relates to methods for preparing such ligands and to compounds which are useful intermediates in such methods. The invention further relates to pharmaceutical compositions comprising such ligands and methods for preparing such pharmaceutical compositions.

Gastrin and the cholecystokinins are structurally related neuropeptides which exist in gastrointestinal tissue and the central nervous system (Mutt V., *Gastrointestinal Hormones*, Glass G. B. J., ed., Raven Press, New York, p. 169; Nisson G., ibid., p. 127).

Gastrin is one of the three primary stimulants of gastric acid secretion. Several forms of gastrin are found including 34-, 17- and 14-amino acid species with the minimum active fragment being the C-terminal tetrapeptide (TrpMetAspPhe-$NH_2$) which is reported in the literature to have full pharmacological activity (Tracey H. J. and Gregory R. A., *Nature* (London), 1964, 204, 935). Much effort has been devoted to the synthesis of analogues of this tetrapeptide (and the N-protected derivative Boc-TrpMetAspPhe-$NH_2$) in an attempt to elucidate the relationship between structure and activity.

Natural cholecystokinin is a 33 amino acid peptide (CCK-33), the C-terminal 5 amino acids of which are identical to those of gastrin. Also found naturally is the C-terminal octapeptide (CCK-8) of CCK-33.

The cholecystokinins are reported to be important in the regulation of appetite. They stimulate intestinal mobility, gall bladder contraction, pancreatic enzyme secretion and are known to have a trophic action on the pancreas. They also inhibit gastric emptying and have various effects in the central nervous system.

Compounds which bind to cholecystokinin and/or gastrin receptors are important because of their potential pharmaceutical use as antagonists or partial agonists of the natural peptides.

A number of gastrin antagonists have been proposed for various therapeutic applications, including the prevention of gastrin-related disorders, gastrointestinal ulcers, Zollinger-Ellison syndrome, antral G cell hyperplasia and other conditions in which lower gastrin activity or lower acid secretion is desirable. The hormone has also been shown to have a trophic action on cells and so an antagonist may be expected to be useful in the treatment of cancers, particularly in the stomach and the colon.

Possible therapeutic uses for cholecystokinin antagonists include the control of appetite disorders such as anorexia nervosa and the treatment of pancreatic inflammation, biliary tract disease and various psychiatric disorders. Other possible uses are in the potentiation of opiate (for example morphine) analgesia and in the treatment of cancers, especially of the pancreas. Moreover, ligands for cholecystokinin receptors in the brain (so-called $CCK_2$ receptors) have been claimed to possess anxiolytic activity.

PCT/GB99/03733 describes a class of compounds having gastrin antagonist activity. This class of compounds is typically characterised by a 5-membered ring, preferably an imidazole or pyrrole, having two hydrocarbyl substituents and an amide or urea-type substituent.

According to the present invention, there are provided compounds of formula (I)

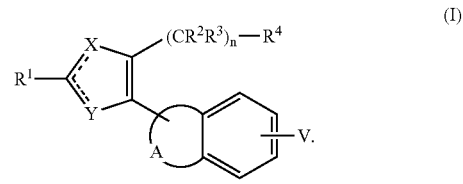

wherein X and Y are independently =N—, —N($R^5$)— ($R^5$ being selected from H, Me, Et, Pr, Bn, OH and —$CH_2COOR^6$, wherein $R^6$ represents H, Me, Et, Pr or Bn), =CH—, —O— or —S—; n is from 1 to 4;

A is an optionally substituted 5- or 6-membered carbocyclic ring wherein
(a) 1 or 2 C atoms may optionally be replaced by N, O and/or S atoms,
(b) A is fused with the aromatic group in formula (I) to form a fused bicycle, and
(c) the ring containing X and Y is linked to a C atom of A;

$R^1$ is H or $C_1$ to $C_{15}$ hydrocarbyl wherein up to three C atoms may optionally be replaced by N, O and/or S atoms and up to three H atoms may optionally be replaced by halogen atoms;

$R^2$ is selected from H, Me, Et, Pr and OH, each $R^2$ being independently selected from H, Me, Et, Pr and OH when n is greater than 1;

$R^3$ (when n is 1) is selected from H, Me, Et and Pr; or (when n is greater than 1) each $R^3$ is independently selected from H, Me, Et and Pr, or two $R^3$ groups on neighbouring carbon atoms are linked to form a $C_3$ to $C_6$ carbocylic ring, or two $R^3$ groups are absent from neighbouring carbon atoms which are linked by a double bond; or $R^2$ and $R^3$ on the same carbon atom together represent an =O group;

$R^4$ is $C_1$ to $C_{15}$ hydrocarbyl wherein up to two C atoms may optionally be replaced by N, O and/or S atoms and up to three H atoms may optionally be replaced by halogen atoms;

V is —CO—NH—$SO_2$—Ph, —$SO_2$—NH—CO—Ph, —$CH_2OH$, or a group of the formula —$R^7U$, (wherein U is —COOH, tetrazolyl, —CONHOH or —$SO_3H$; and $R^7$ is a bond; $C_1$ to $C_6$ hydrocarbylene, optionally substituted by hydroxy, amino or acetamido; —O—($C_1$ to $C_3$ alkylene)-; —$SO_2NR^8$—$CHR^9$—; —CO—$NR^8$—$CHR^9$—, $R^8$ and $R^9$ being independently selected from H and methyl; or —NH—$(CO)_c$—$CH_2$—, c being 0 or 1);

or a pharmaceutically acceptable salt thereof.

Preferably, compounds of this invention are defined by formula (Ia) or (Ib).

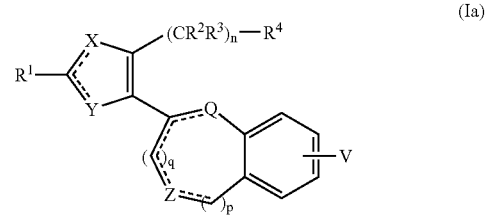

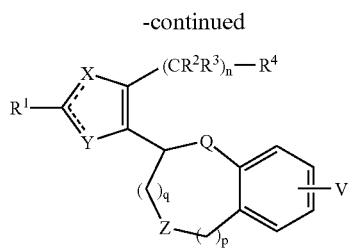

wherein
X, Y, n, $R^1$, $R^2$, $R^3$, $R^4$ and V are defined as above;
p=0 or 1;
q=0 or 1;
Z and Q are independently =N—, —NH—, =CH—, —$CH_2$—, —S— or —O—; provided that p+q≠2; and
when p+q=1 in formula (Ia), at least one of Z or Q is =N— or =CH—.

Accordingly, certain fused bicycles which are contemplated in the present invention are those derived from napthalene, benzimidazole, benzoxazole, benzothiazole, benzothiophene, isobenzothiophene, benzofuran, isobenzofuran, indole, isoindole, chromene, isochromene, quinoline, isoquinoline, quinoxaline, quinazoline, chroman, isochroman, indoline or isoindoline.

Most preferably, the fused bicycles are derived from benzimidazole or benzoxazole.

Preferably X is =N— and Y is —NH—, or vice versa.

Preferably $R^1$ is $C_1$ to $C_{12}$ hydrocarbyl wherein one C atom may optionally be replaced by N or O and up to three H atoms may optionally be replaced by F, Cl or Br. More preferably $R^1$ is $C_3$ to $C_{12}$ alicyclic; phenyl, pyridyl, phenyl $C_1$–$C_3$ alkyl or pyridyl $C_1$–$C_3$ alkyl (all optionally substituted with OMe, $NMe_2$, $CF_3$, Me, F, Cl, Br or I); or $C_1$ to $C_8$ alkyl. Alicyclic groups include $C_5$ to $C_8$ cycloalkyl, $C_7$ to $C_{10}$ polycycloalkyl, $C_5$ to $C_8$ cycloalkenyl and $C_7$ to $C_{10}$ polycycloalkenyl, all optionally substituted with methyl. Phenyl $C_1$–$C_3$ alkyl includes, for example, benzyl.

Most preferably $R^1$ is cyclohexyl or bicyclooctyl.

V may be substituted at any one of the positions shown below.

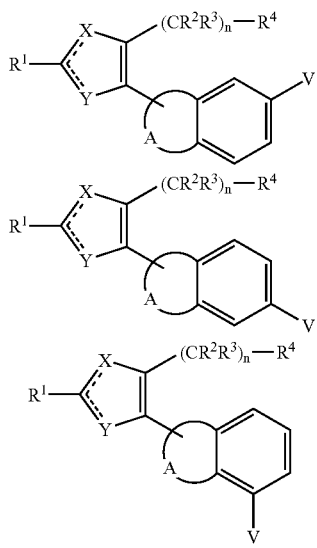

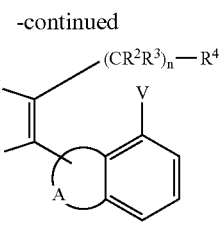

Preferably V is —CO—NH—$SO_2$—Ph, —$SO_2$—NH—CO—Ph, —$OCH_2COOH$, tetrazolyl or $(CH_2)_S COOH$, wherein S is from 0, 1 or 2. Most preferably V is $CH_2COOH$, COOH or tetrazolyl.

In certain compounds according to the present invention $R^2$ and $R^3$ are H, and n is from 1 to 3.

In a further group of compounds according to this invention $R^2$ and $R^3$ together form an =O group and n is 1.

In certain compounds according to this invention $R^4$ is $C_3$ to $C_{15}$ carbocyclic, optionally substituted with up to three halogen atoms. Preferably $R^4$ is adamantyl, cycloheptyl, cyclohexyl or phenyl. Most preferably $R^4$ is adamantyl.

In a further group of compounds according to this invention $R^4$ is —NH—$R^{10}$ or —O$R^{10}$, in which $R^{10}$ is $C_3$ to $C_{12}$ carbocyclic, optionally substituted with up to three halogen atoms.

Preferably $R^{10}$ is adamantyl, cycloheptyl, cyclohexyl or phenyl. Most preferably $R^{10}$ is adamantyl.

Certain compounds of the present invention exist in various regioisomeric, enantiomeric, tautomeric and diastereomeric forms. It will be understood that the invention comprehends the different regioisomers, enantiomers, tautomers and diastereomers in isolation from each other as well as mixtures.

Compounds of the present invention according to formula (Ia) wherein
(i) p is 0
(ii) q is 0
(iii) X is —NH—
(iv) Y is =N—
(v) Q is —O— or —NH—
(vi) Z is =N— may be conveniently prepared by the route exemplified in Reaction Scheme 1.

Reaction Scheme 1

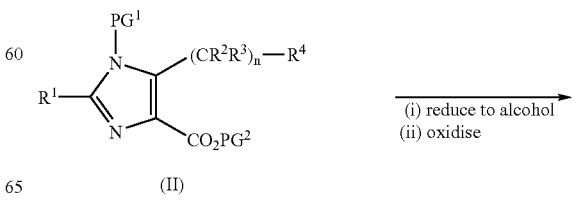

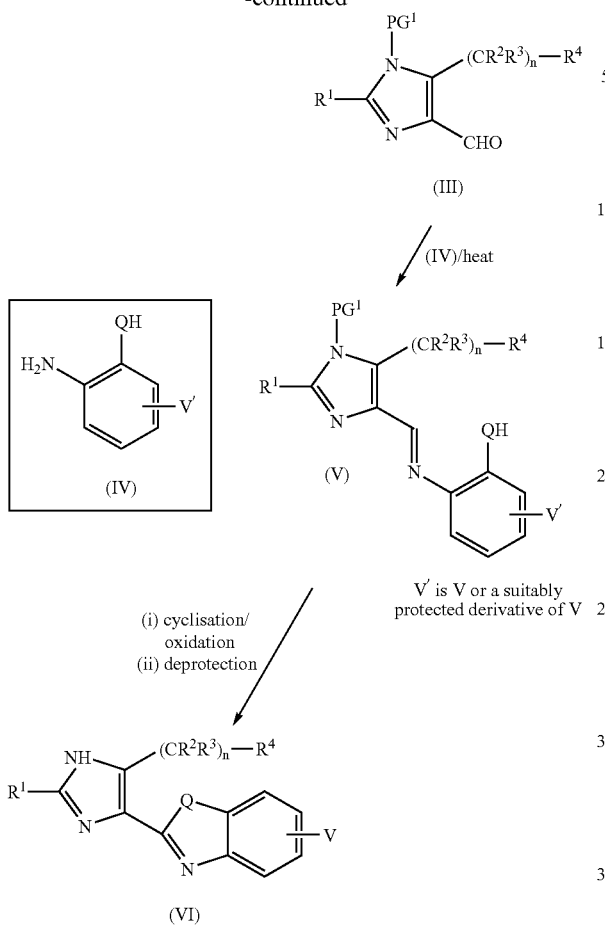

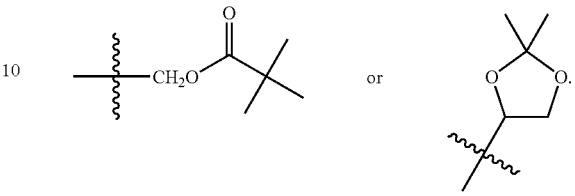

Suitably protected aldehyde (III) was prepared from imidazole ester (II) using standard reduction/oxidation chemistry e.g. LiAlH$_4$ reduction of a benzyl ester followed by oxidation with MnO$_2$. A Mannich condensation of aldehyde (III) with amine (IV) furnishes imine (V). Finally, heating, oxidation (with for example NiO$_2$) and deprotection affords the requisite fused bicycle (VI). It will be readily apparent to the skilled person that other compounds according to formula (I), (Ia) or (Ib) can be prepared by known heterocycle syntheses starting from aldehyde (III), or suitable derivatives thereof.

Hence, the present invention provides methods of making compounds according to formula (I).

The invention also comprehends derivative compounds ("pro-drugs") which are degraded in vivo to yield the species of formula (I). Pro-drugs are usually (but not always) of lower potency at the target receptor than the species to which they are degraded. Pro-drugs are particularly useful when the desired species has chemical or physical properties which make its administration difficult or inefficient. For example, the desired species may be only poorly soluble, it may be poorly transported across the mucosal epithelium, or it may have an undesirably short plasma half-life. Further discussion of pro-drugs may be found in Stella, V. J. et al., "Prodrugs", *Drug Delivery Systems*, 1985, pp. 112–176, and Drugs, 1985, 29, pp. 455–473.

Pro-drug forms of the pharmacologically-active compounds of the invention will generally be compounds according to formula (1) having an acid group which is esterified or amidated. Included in such esterified acid groups are groups of the form —COOR$^a$, wherein R$^a$ is C$_1$ to C$_5$ alkyl, phenyl, substituted phenyl, benzyl, substituted benzyl, or one of the following:

Amidated acid groups include groups of the formula —CONR$^b$R$^c$, wherein R$^b$ is H, C$_1$ to C$_5$ alkyl, phenyl, substituted phenyl, benzyl, or substituted benzyl, and R$^c$ is —OH or one of the groups just recited for R$^b$.

Compounds of formula (I) having an amino group may be derivatised with a ketone or an aldehyde such as formaldehyde to form a Mannich base. This will hydrolyse with first order kinetics in aqueous solution.

Another aspect of the present invention is a pharmaceutical composition comprising a compound of formula (I) substantially as described herein before with a pharmaceutically acceptable diluent or carrier.

Yet another aspect of the present invention is a method of making a pharmaceutical composition comprising a compound of formula (I) substantially as described herein before, comprising mixing said compound with a pharmaceutically acceptable diluent or carrier.

Pharmaceutically acceptable salts of the acidic or basic compounds of the invention can of course be made by conventional procedures, such as by reacting the free base or acid with at least a stoichiometric amount of the desired salt-forming acid or base.

Pharmaceutically acceptable salts of the acidic compounds of the invention include salts with inorganic cations such as sodium, potassium, calcium, magnesium, and zinc, and salts with organic bases. Suitable organic bases include N-methyl-D-glucamine, arginine, benzathine, diolamine, olamine, procaine and tromethamine.

Pharmaceutically acceptable salts of the basic compounds of the invention include salts derived from organic or inorganic acids. Suitable anions include acetate, adipate, besylate, bromide, camsylate, chloride, citrate, edisylate, estolate, fumarate, gluceptate, gluconate, glucuronate, hippurate, hyclate, hydrobromide, hydrochloride. iodide, isethionate, lactate, lactobionate, maleate, mesylate, methylbromide, methylsulfate, napsylate, nitrate, oleate, pamoate, phosphate, polygalacturonate, stearate, succinate, sulfate, sulfosalicylate, tannate, tartrate, terephthalate, tosylate and triethiodide.

It is anticipated that the compounds of the invention can be administered by oral or parenteral routes, including intravenous, intramuscular, intraperitoneal, subcutaneous, rectal and topical administration, and inhalation.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate and lactose. Corn starch and alginic acid are suitable disintegrating agents. Binding agents may include starch and gelatine. The lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatine capsules in which the active ingredient is mixed with a solid diluent and soft gelatine capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Effective doses of the compounds of the present invention may be ascertained by conventional methods. The specific dosage level required for any particular patient will depend on a number of factors, including severity of the condition being treated, the route of administration and the weight of the patient. In general, however, it is anticipated that the daily dose (whether administered as a single dose or as divided doses) will be in the range 0.001 to 5000 mg per day, more usually from 1 to 1000 mg per day, and most usually from 10 to 200 mg per day. Expressed as dosage per unit body weight, a typical dose will be expected to be between 0.01 µg/kg and 50 mg/kg, especially between 10 µg/kg and 10 mg/kg, eg. between 100 µg/kg and 2 mg/kg.

In a further aspect of the present invention there are provided pharmaceutical compositions comprising a compound according to formula (I) and a proton pump inhibitor. Compositions comprising a CCK/gastrin antagonist and a proton pump inhibitor are described in International patent application WO93/12817, incorporated herein by reference.

In one aspect of the present invention the proton pump inhibitor is
  omeprazole which is 5-methoxy-2-[[(4-methoxy-3,5-dimethyl-2-pyridinyl)-methyl]sulfinyl]-1H-benzimidazole;
  BY308;
  SK & 95601 which is 2-[[(3-chloro-4-morpholino-2-pyridyl)methyl]sulfinyl]-5-methoxy-(1H)-benzimidazole;
  SK & 96067 which is 3-butyryl-4-(2-methylphenylamino)-8-methoxyquinoline;
  5-trifluoromethyl-2-[4-methoxy-3-methyl-2-pyridyl-methyl]-thio-[1H]-benzimidazole;

or pharmaceutically acceptable salts thereof.

These proton pump inhibitors are described and claimed in U.S. Pat. Nos. 4,472,409 and 4,255,431. These patents are incorporated herein by reference.

In a further aspect of the present invention, the proton pump inhibitor is
  lansoprazole which is 2-[[[3-methyl4(2,2,2-trifluoroethoxy)-2-pyridinyl]methyl]sulfinyl]-1H-benzimidazole;
  pantoprazole which is 5-(difluoromethoxy)-2-[[(3,4-dimethoxy-2-pyridinyl)methyl]sulfinyl]-1H-benzimidazole;
  perprazole;

rabeprazole which is 2-[[4-(3-methoxypropoxy)-3-methylpyridin-2-yl]methylsulfinyl]-1H-benzimidazole;
[[4-(2,2,2-trifluoroethoxy)-3-methyl-2-pyridyl]-methyl] sulfenamide;
(Z)-5-methyl-2-[2-(1-naphthyl)ethenyl]-4-piperidinopyridine HCl;
2-(4-cyclohexyloxy-5-methylpyridin-2-yl)-3-(1-naphthyl)-1-propanol;
methyl 2-cyano-3-(ethylthio)-3-(methylthio)-2propenoate;
2-((4-methoxy-2-pyridyl)methylsulphinyl)-5-(1,1,2,2-tetrafluoroethoxy)-1H-benzimidazole sodium;
2-[[[4-(2,2,3,3,4,4,4-heptafluorobutoxy)-2-pyridyl]methyl]sulfinyl]-1H-thieno [3,4-d]imidazole;
2-[[[4-(2,2,2-trifluoroethoxy)-3-methyl-2-pyridyl]methyl]sulfinyl]-1H-benzimidazole;
2-[[[4-(2,2,2-trifluoroethoxy)-3-methyl-2-pyridyl]methyl]sulfinyl]-1H-benzimidazole;
2-methyl-8-(phenylmethoxy)-imidazo(1,2-A)-pyridine-3-acetonitrile;
(2-((2-dimethylaminobenzyl)sulfinyl)-benzimidazole);
4-(N-allyl-N-methylamino)-1-ethyl-8-((5-fluoro-6-methoxy-2-benzimidazolyl) sulfinylmethyl)-1-ethyl 1,2,3,4-tetrahydroquinolone;
2-[[(2-dimethylaminophenyl)methyl]sulfinyl]-4,7-dimethoxy-1H-benz imidazole;
2-[(2-(2-pyridyl)phenyl)sulfinyl)-1H-benzimidazole;
(2-[(2-amino-4-methylbenzyl)sulfinyl]-5-methoxybenzo[d]imidazole;
(4(2-methylpyrrol-3-yl)-2-guanidisothiazole);
4-(4-(3-(imidazole)propoxy)phenyl)-2phenylthiazole;
(E)-2-(2-(4-(3-(dipropylamino)butoxy)phenyl)-ethenyl) benzoxazole;
(E)-2-(2-(4-(3-(dipropylamino)propoxy)phenyl)ethenyl)-benzothiazole;
Benzeneamine, 2-[[(5-methoxy-1H-benzimidazol-2-yl) sulfinyl]methyl)-4-methyl-;
Purilacidin A;
2,3-dihydro-2-methoxycarbonylamino-1,2-benzisothiazol-3-one;
2-(2-ethylaminophenylmethylsulfinyl)-5,6-dimethoxybenzimidazole;
2-methyl-8-(phenylmethoxy)imidazo[1,2-a]pyridine-3-acetonitrile;
3-amino-2-methyl-8-phenylmethoxyimidazo[1,2-a)-pyrazine HCl;
2-[[(3-chloro-4-morpholino-2-pyridyl)methyl]-sulfinyl)-5-methoxy-(1H)-benzinidazole;
[3-butyryl-4-(2-methylphenylamino)-8-methoxy-quinoline);
2-indanyl 2-(2-pyridyl)-2-thiocarbamoylacetate HCl;
2,3-dihydro-2-(2-pyridinyl)-thiazolo (3,2-a)-benzimidazole;
3-cyanomethyl-2-methyl-8-(3-methyl-2-butenyloxy)-(1,2-a)imidazopyridine;
zinc L-carnosine;

or pharmaceutically acceptable salts thereof.

Rabeprazole is described in U.S. Pat. No. 5,045,552. Lansoprazole is described in U.S. Pat. No. 4,628,098. Pantoprazole is described in U.S. Pat. No. 4,758,579. These patents are incorporated herein by reference.

Preferably, the proton pump inhibitor is selected from (RS)-rabeprazole, (RS)-omeprazole, lansoprazole, pantoprazole, (R)-omeprazole, (S)-omeprazole, perprazole, (R)-rabeprazole, (S)-rabeprazole, or the alkaline salts thereof. The alkaline salts may be, for example, the lithium, sodium, potassium, calcium or magnesium salts.

Compositions of this invention comprising a compound of formula (I) and a proton pump inhibitor may be administered as described above. Preferably the dose of each of the active ingredients in these compositions will be equal to or less than that which is approved or indicated in monotherapya with said active ingredient.

In another aspect of this invention, there is provided a kit comprising a compound of formula (I) and a proton pump inhibitor. The kit is useful as a combined preparation for simultaneous, separate or sequential use in the treatment of patients suffering from gastrointestinal disorders.

In yet a further aspect of the present invention there is provided a method of making a pharmaceutical composition comprising a compound of formula (I) substantially as described herein before and a proton pump inhibitor, comprising mixing said compound and said proton pump inhibitor with a pharmaceutically acceptable carrier or diluent.

The term "hydrocarbyl" is used herein to refer to monovalent groups consisting of carbon and hydrogen. Hydrocarbyl groups thus include alkyl, alkenyl and alkynyl groups (in both straight and branched chain forms), cycloalkyl (including polycycloalkyl), cycloalkenyl and aryl groups, and combinations of the foregoing, such as alkylcycloalkyl, alkylpolycycloalkyl, alkylaryl, alkenylaryl, alkynylaryl, cycloalkylaryl and cycloalkenylaryl groups.

Where reference is made to a carbon atom of a hydrocarbyl group being replaced by a N, O or S atom, what is intended is that

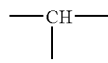

is replaced by

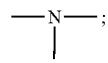

or that —CH$_2$— is replaced by —O— or —S—.

A "carbocyclic" group, as the term is used herein, comprises one or more closed chains or rings, which consist entirely of carbon atoms. Carbocyclic groups thus include aryl groups (such as phenyl, naphthyl, indanyl, fluorenyl, (1,2,3,4)-tetrahydronaphthyl, indenyl and isoindenyl, and substituted derivatives thereof), and also alicyclic groups. The term "alicyclic group" refers to a carbocyclic group which does not contain an aromatic ring, and thus includes groups such as cyclopropyl, cyclobutyl, cyclopentyl, cyclohexyl, cyclohexenyl, adamantyl, norbornyl, bicyclo[2.2.2]octyl, norbornenyl and bicyclo[2.2.2]octenyl, and also groups (such as adamantanemethyl and methylcyclohexyl) which contain both alkyl or alkenyl groups in addition to cycloalkyl or cycloalkenyl moieties.

The term "aryl" is used herein to refer to an aromatic group, such as phenyl or naphthyl, or a heteroaromatic group, such as pyridyl, pyrrolyl, or furanyl.

The term "alkyl" is used herein to refer to both straight and branched chain forms.

When reference is made herein to a substituted carbocyclic group (such as substituted phenyl) or a substituted heterocyclic group, the substituents are preferably from 1 to 3 in number and selected from $C_1$ to $C_6$ allyl, $C_1$ to $C_6$ alkoxy, thio, $C_1$ to $C_6$ alkylthio, carboxy, carboxy($C_1$ to $C_6$)alkyl, formyl, $C_1$ to $C_6$ alkylcarbonyl, $C_1$ to $C_6$ alkylcarbonylalkoxy, nitro, trihalomethyl, hydroxy, $C_1$ to $C_6$ alkylhydroxy, hydroxy($C_1$ to $C_6$)alkyl, amino, $C_1$ to $C_6$ alkylamino, di($C_1$ to $C_6$ alkyl)amino, aminocarboxy, $C_1$ to $C_6$ alkylaminocarboxy, di($C_1$ to $C_6$ alkyl)aminocarboxy, aminocarboxy($C_1$ to $C_6$)alkyl, $C_1$ to $C_6$ alkylaminocarboxy($C_1$ to $C_6$)alkyl, di($C_1$ to $C_6$ alkyl)aminocarboxy($C_1$ to $C_6$)alkyl, $C_1$ to $C_6$ alkylcarbonylamino, $C_5$ to $C_8$ cycloalkyl, $C_5$ to $C_8$ cycloaLkyl($C_1$ to $C_6$)alkyl, $C_1$ to $C_6$ alkylcarbonyl($C_1$ to $C_6$ alkyl)amino, aryl, aryl($C_1$ to $C_6$)alkyl, ($C_1$ to $C_6$ alkyl)aryl, halo, $C_1$ to $C_6$ alkylhalo, sulphamoyl, tetrazolyl and cyano.

Most usually, substituents will be selected from $C_1$ to $C_6$ alkyl, $C_1$ to $C_6$ alkoxy, thio, $C_1$ to $C_6$ alkylthio, carboxy, carboxy($C_1$ to $C_6$)alkyl, formyl, $C_1$ to $C_6$ alkylcarbonyl, $C_1$ to $C_6$ alkylcarbonylalkoxy, nitro, trihalomethyl, hydroxy, $C_1$ to $C_6$ alkylhydroxy, hydroxy($C_1$ to $C_6$)alkyl, amino, $C_1$ to $C_6$ alkylamino, di($C_1$ to $C_6$ alkyl)amino, aminocarboxy, $C_1$ to $C_6$ alkylaminocarboxy, di($C_1$ to $C_6$ alkyl)aminocarboxy, aminocarboxy($C_1$ to $C_6$)alkyl, $C_1$ to $C_6$ alkylaminocarboxy($C_1$ to $C_6$)alkyl, di($C_1$ to $C_6$ alkyl)aminocarboxy($C_1$ to $C_6$)alkyl, $C_1$ to $C_6$ alkylcarbonylamino, $C_5$ to $C_8$ cycloalkyl, $C_5$ to $C_8$ cycloalkyl($C_1$ to $C_6$)alkyl, $C_1$ to $C_6$ alkylcarbonyl($C_1$ to $C_6$ alkyl)amino, halo, $C_1$ to $C_6$ alkylhalo, sulphamoyl, tetrazolyl and cyano.

The term "halogen" is used herein to refer to any of fluorine, chlorine, bromine and iodine. Most usually, however, halogen substituents in the compounds of the invention are chlorine and fluorine substituents.

The term "suitably protected" used herein refers to the use of any suitable protecting group to protect a functional group. Such protecting groups are denoted as PG, PG$^1$, PG$^2$, PG3 etc. in the Reaction Scheme illustrated above. Suitable protecting groups will be readily apparent to the skilled person and may be found in, for example, Kocienski, *Protecting Groups*, Thieme, New York, 1994. For example, in the case of hydroxyl groups, suitable protecting groups may include esters, ethers (e.g. silyl ethers or alkyl ethers) or acetals. Some specific examples of typical hydroxyl protecting groups are allyl, Aloc, benzyl, BOM, t-butyl, trityl, TBS, TBDPS, TES, TMS, TIPS, PMB, MEM, MOM, MTM, and THP. In the case of nitrogen atoms, suitable protecting groups may include Boc, Aloc, Troc, benzyl, allyl, Fmoc or silyl. In the case of carboxylic acids, suitable protecting groups may include esters (e.g. benzyl, allyl, methyl or ethyl esters).

The invention is now further illustrated by means of the following Examples. All reactions were performed under an atmosphere of dry argon unless otherwise stated. Anhydrous dichloromethane (DCM) was freshly distilled from calcium hydride. Anhydrous tetrahydrofuran (THF) and N,N-dimethylformamide (DMF) were used.

EXAMPLE 1

2-[5-(Adamantan-1-yloxymethyl)-2-cyclohexyl-1H-imidazole-4-yl]-benzooxazole-5-carboxylic acid Step a. (Adamantan-1-yloxy)-acetic acid. A mixture of (adamantan-1-yloxy)-acetic acid ethyl ester (A. F. Noels et al. Tetrahedron, 1982, 38, 2733) (7.29 g, 29 mmol) and potassium hydroxide (2.60 g, 46 mmol) in water-ethanol (1:2 mixture, 180 ml) was heated at reflux for 2 h. The mixture was cooled, then concentrated in vacuum and acidified with concentrated hydrochloric acid. The resultant white precipitate was dissolved in ethyl acetate (200 ml).

The solution was washed with brine (2×200 ml), dried (MgSO$_4$) and the solvent was evaporated to afford a white crystalline solid (5.85 g 92%). $^1$H NMR (300 MHz, CDCl$_3$) 4.08 (2H, s), 2.20–1.58 (15H, m).

Step b. 4-(Adamantan-1-yloxy)-3-oxo-2-(triphenyl-l$^5$-phosphanylidene)-butyric acid benzyl ester. Oxalyl chloride (18.6 ml, 0.214 mol) was added to a solution of the product of step a (39.13 g, 0.178 mol) in DCM (800 ml) containing catalytic amount of DMF at room temperature. The mixture was stirred at ambient temperature for 1 h, then the solvent was evaporated. The residue was dissolved in benzene (100 ml) and added dropwise to a solution of benzyl(triphenylphosphoranylidene)acetate (72.9 g, 0.178 mol) and N,O-bis(trimethylsilyl)acetamide (53.2 ml, 0.215 mol) in benzene (300 ml) at 0° C. The mixture was allowed to warm to room temperature, and stirred for 16 h. The reaction mixture was diluted with ethyl acetate (500 ml), washed with 5% aqueous potassium hydrogen sulfate (500 ml), 10% sodium carbonate (500 ml), brine (300 ml), dried (MgSO$_4$) and the solvent was evaporated. The residue was triturated with diethyl ether to afford a white solid (93.83 g, 98%). $^1$H NMR (300 MHz, CDCl$_3$) 7.64–6.94 (20H, m), 4.74 (2H, s), 4.72 (2H, s), 2.08–1.57 (15H, m).

Step c. 5-(Adamantan-1-yl-oxymethyl)-2-cyclohexyl-1H-imidazole-4-carboxylic acid benzyl ester. To a vigorously stirred solution of the product of step b (33.0 g, 55.0 mmol) in DCM/water (1:1 mixture, 800 ml) were added tetrabutylammonium bromide (1.77 g, 5.50 mmol) and potassium peroxymonosufate (OXONE) (67.4 g, 110 mmol) at 0° C. The mixture was stirred at ambient temperature for 48 h, the organic layer was separated, washed with water (3×200 ml), brine (200 ml), dried (MgSO$_4$) and the solvent was evaporated in vacuum. To a slurry of the residue (1:1 mixture of 4-(adamantan-1-yloxy)-2,3-dioxo-butyric acid benzyl ester monohydrate and triphenylphosphine oxide) and ammonium acetate (42.4 g, 550 mmol) in acetic acid (250 ml) was added cyclohexanecarboxaldehyde (8.0 ml, 66.0 mmol). The mixture was stirred in an oil bath heated at 70° C. for 2 h. The solution was cooled to room temperature and the acetic acid was evaporated in vacuum. The residue was suspended in ethyl acetate (200 ml) and the precipitated ammonium acetate was filtered and washed with ethyl acetate (2×50 ml). The filtrate was washed with saturated sodium bicarbonate (2×200 ml) and brine (200 ml). The organic layer was dried (MgSO$_4$) and the solvent was evaporated. The crude product was purified by flash column chromatography (silica, DCM/ethyl acetate 4:1) to afford a pale orange foam, which was recrystallized from hexane-ethyl acetate 1:1 to afford the product as an off-white solid (13.6 g, 55%). $^1$H NMR (CDCl$_3$) 7.40 (5H, m), 5.30 (2H, s), 4.76 (2H, br s), 2.79 (1H, m), 2.14 (3H, br s), 2.05 (2H, m), 1.85–1.26 (20H, m).

Step d. 5-(Adamantan-1-yloxymethyl)-1-benzyl-2-cyclohexyl-1H-imidazole-4-carboxylic acid benzyl ester. To the solution of the product of step c (2.1 g, 4.69 mmol) in DMF (15 ml) was added sodium hydride (60% dispersion in mineral oil, 225 mg, 5.62 mmol). The mixture was stirred at ambient temperature for 0.5 h then benzyl bromide (0.67 ml, 5.62 mmol) was added. The reaction mixture was stirred at ambient temperature for 16 h, then partitioned between ethyl acetate and water. The organic layer was washed with 1M HCl, saturated sodium hydrogen carbonate, and brine, dried (MgSO$_4$) and evaporated. The major isomer was isolated by flash chromatography (silica, DCM/ethyl acetate 92:8) (2.15 g, 85%). $^1$H NMR (300 MHz, CDCl$_3$) 7.45 (2H, dd), 7.37–7.27 (6H, m), 6.98 (2H, m), 5.37 (2H, s), 5.28 (2H, s), 4.68 (2H, s), 2.52 (1H, m), 2.14 (2H, br s), 2.04 (3H, br s), 1.78–1.35 (17H, m), 1.28–1.14 (3H, m).

Step e. [5-(Adamantan-1-yloxymethyl)-1-benzyl-2-cyclohexyl-1H-imidazole-4-yl]-methanol. Lithium aluminium hydride (300 mg, 8.20 mmol) was added in small portions to an ice cooled solution of the product of step d (2.20 g, 4.10 mmol) in THF (25 ml). The suspension was allowed to warm to ambient temperature and stirred for 2 h. The reaction mixture was cooled with ice and sodium hydroxide solution (2N, 1.6 ml) was slowly added. The reaction mixture was diluted with ethyl acetate (50 ml) and filtered through a plug of Celite and MgSO$_4$. The filtrate was evaporated under reduced pressure and the residue was crystallised from diethyl ether to afford white crystals (1.40 g, 79%). $^1$H NMR (300 MHz, CDCl$_3$) 7.28 (3H, m), 7.00 (2H, m), 5.18 (2H, s), 4.63 (2H, d), 4.34 (2H, s), 2.64 (1H, br m), 2.50 (1H, m), 2.13 (3H, br s), 1.72–1.54 (19H, m), 1.25 (3H, m).

Step f. 5-(Adamantan-1-yloxymethyl)-1-benzyl-2-cyclohexyl-1H-imidazole-4-carbaldehyde. To a solution of the product of step e (1.40 g, 3.22 mmol) in dioxan (40 ml) was added manganese(IV) oxide (1.45 g, 16.7 mmol) and the mixture was stirred at ambient temperature for 3 h. The reaction mixture was filtered through Celite and the filtrate was evaporated to afford a colourless foam (1.38 g, 99%). $^1$H NMR (300 MHz, CDCl$_3$) 9.99 (1H, s), 7.32 (3H, m), 7.00 (2H, d), 5.31 (2H, s), 4.74 (2H, s), 2.51 (1H, m), 2.13 (3H, br s), 1.78–1.57 (19H, m), 1.22 (3H, m).

Step g. 3-{[5-(Adamantan-1-yloxymethyl)-1-benzyl-2-cyclohexyl-1H-imidazole-4-ylmethylene]-amino}-4-hydroxy-benzoic acid methyl ester. To a solution of the product of step f (432 mg, 1.00 mmol) in ethanol (5 ml) was added 3-amino-4-hydroxy-benzoic acid methyl ester. The mixture was heated at reflux for 5 min, then left to stand at ambient temperature for 16 h. The crystals were filtered, washed with ethanol and dried (470 mg, 81%). $^1$H NMR (300 MHz, CDCl$_3$) 8.83 (1H, s), 7.99 (1H, s), 7.86 (1H, dd), 7.35 (3H, m), 7.02 (3H, m), 5.30 (2H, s), 4.75 (2H, s), 3.89 (3H, s), 2.55 (1H, m), 2.15 (3H, br s), 1.81–1.55 (19H, m), 1.25 (3H, m).

Step h. 2-[5-(Adamantan-1-yloxymethyl)-1-benzyl-2-cyclohexyl-1H-imidazole-4-yl]-benzooxazole-5-carboxylic acid methyl ester. To a solution of the product of step g (310 mg, 0.53 mmol) in DCM (10 ml) was added nickel peroxide (500 mg). The mixture was stirred at ambient temperature for 3 h, filtered through Celite and the filtrate was evaporated under reduced pressure. The crude product was purified by flash column chromatography (silica, DCM/ethyl acetate 95:5) to afford white solid (200 mg, 65%). $^1$H NMR (300 MHz, CDCl$_3$) 8.39 (1H, s), 8.04 (1H, dd), 7.61 (1H, d), 7.34 (3H, m), 7.05 (3H, d) 5.37 (2H, s), 5.01 (2H, s), 3.96 (3H, s), 2.59 (1H, m), 2.15 (3H, br s), 1.84–1.56 (19H, m), 1.24 (3H, m).

Step i. 2-[5-(Adamantan-1-yloxymethyl)-2-cyclohexyl-1H-imidazole-4-yl]-benzooxazole-5-carboxylic acid methyl ester. To a solution of the product of step h (197 mg, 0.34 mmol) in acetic acid (5 ml) was added 10% palladium on charcoal (20 mg). The mixture was stirred under a hydrogen atmosphere for 16 h. The catalyst was filtered, the filtrate was evaporated under reduced pressure. The residual acetic acid was removed by co-evaporation with toluene and then chloroform to afford a white solid (165 mg, 99%). $^1$H NMR (300 MHz, CDCl$_3$) 9.35 (1H, br s), 8.40 (1H, s), 8.04 (1H, d), 7.59 (1H, d), 5.06 (2H, s), 3.95 (3H, s) 2.82 (1H, m), 2.22 (3H, br s), 2.11 (2H, m), 1.88 (6H, br s), 1.72–1.57 (11H, m), 1.42–1.26 (3H, m).

Step k. To a solution of the product of step i (165 mg, 0.34 mmol) in THF (3 ml) was added lithium hydroxide monohydrate (70 mg, 1.68 mmol) and water (1.5 ml). The mixture was stirred at ambient temperature for 16 h, then heated at reflux for 3 h. The THF was removed by evaporation under reduced pressure, the residue was diluted with water and acidified (1N HCl, pH=3). The precipitate was filtered, washed with water, dried to afford a beige solid (117 mg, 74%). $^1$H NMR (300 MHz, d$_6$-DMSO) 13.00 (2H, br s), 8.20 (1H, s), 7.98 (1H, d), 7.80 (1H, d), 4.87 (2H, s), 2.77 (1H, m), 2.12 (3H, br s), 1.95–1.58 (19H, m), 1.31 (3H, m). The acid was converted to the N-methyl-D-glucamine salt and lyophilised from water/dioxan. Found: C, 57.84, H, 7.87, N, 7.69%; C$_{35}$H$_{50}$N$_4$O$_9$.2.2H$_2$O requires: C, 57.78, H, 7.80, N, 7.70%.

EXAMPLE 2

2-[5-(Adamantan-1-yloxymethyl)-2-cyclohexyl-1H-imidazole-4-yl]-benzooxazole-6-carboxylic acid The title compound was prepared according to the procedure of Example 1, with the modification that 4-amino-3-hydroxy-benzoic acid methyl ester was used in step g instead of 3-amino-4-hydroxy-benzoic acid methyl ester. $^1$H NMR (300 MHz, d$_6$-DMSO) 13.01 (2H, br s), 12.40 (1H, br s), 8.18 (1H, s), 7.95 (1H, d), 7.75 (1H, d), 4.89 (2H, s), 2.73 (1H, m), 2.12 (3H, br s), 1.93 (2H, m), 1.80–1.54 (17H, m), 1.36–1.21 (3H, m). The acid was converted to the N-methyl-D-glucamine salt and lyophilised from water/dioxan. Found: C, 59.60, H, 7.89, N, 8.05%; C$_{35}$H$_{50}$N$_4$O$_9$.2.0H$_2$O requires: C, 59.47, H, 7.70, N, 7.93%.

EXAMPLE 3

2-[5-(Adamantan-1-yloxymethyl)-2-cyclohexyl-1H-imidazole-4-yl]-1H-benzoimidazole-5-carboxylic acid Step a. 2-[5-(Adamantan-1-yloxymethyl)-1-benzyl-2-cyclohexyl-1H-imidazole-4-yl]-1H-benzoimidazole-5-carboxylic acid methyl ester. To a solution of 5-(adamantan-1-yloxymethyl)-1-benzyl-2-cyclohexyl-1H-imidazole-4-carbaldehyde (Example 1, step f) (320 mg, 0.74 mmol) in ethanol (5 ml) was added 3,4-diamino-benzoic acid methyl ester (123 mg, 0.74 mmol). The mixture was heated at reflux for 5 min, then kept at ambient temperature for 16 h. The solvent was evaporated; the residue was dissolved in nitrobenzene (3 ml) and placed in an oil bath at 150° C. for 1 h. The solution was cooled to ambient temperature and purified by flash column chromatography (silica, DCM/ethyl acetate 9:1 to 8:2) to afford a colourless foam (255 mg, 60%). $^1$H NMR (300 MHz, CDCl$_3$) 11.35 and 11.25 (1H, 2×br s), 8.42 and 8.05 (1H, 2×s), 7.90 and 7.70 (2H, 2×m), 7.30 (4H, m), 7.06 (2H, m), 5.29 (2H, s), 5.12 and 5.09 (2H, 2×s), 3.92 (3H, s), 2.50 (1H, m), 2.13 (3H, br s), 1.81–1.55 (19H, m), 1.23 (3H, m).

Step b. 2-[5-(Adamantan-1-yloxymethyl)-2-cyclohexyl-1H-imidazole-4-yl]-1H-benzoimidazole-5-carboxylic acid methyl ester. The product of step a (250 mg, 0.43 mmol) was hydrogenolysed using essentially the same procedure as in Example 1, step i to afford an off-white solid (179 mg, 85%). $^1$H NMR (300 MHz, CDCl$_3$) 8.27 (1H, br s), 7.98 (1H, d), 7.60 (1H, br s), 4.94 (2H, s), 3.95 (3H, s), 2.74 (1H, m), 2.20 (3H, br s), 2.02–1.57 (19H, m), 1.29 (3H, m).

Step c. To a solution of the product of step b (170 mg, 0.35 mmol) in ethanol (3 ml) was added a solution of potassium hydroxide (80 mg, 1.40 mmol) in water. The mixture was heated at reflux for 4 h, cooled and the ethanol was evaporated. The residue was diluted with water (5 ml) and acidified (1N HCl, pH=3). The precipitate was filtered, washed with water and dried to afford an off-white solid (130 mg, 74%). $^1$H NMR (300 MHz, d$_6$-DMSO) 8.19 (1H, s), 7.87 (1H, d), 7.68 (1H, d), 5.00 (2H, s), 2.94 (1H, m), 2.10 (3H, br s), 2.00 (2H, m), 1.78–1.13 (20H, m). The acid was converted to the N-methyl-D-glucamine salt and lyophilised from water/dioxan. Found: C, 59.11, H, 8.00, N, 9.67%; C$_{35}$H$_{51}$N$_5$O$_8$.2.4H$_2$O requires: C, 59.00, H, 7.89, N, 9.83%.

EXAMPLE 4

2-[5-(Adamantan-1-yloxymethyl)-2-cyclohexyl-1H-imidazole-4-yl]-1H-benzoimidazole-4-carboxylic acid Step a. 2,3-Diamino-benzoic acid methyl ester. To a solution of 2-amino-3-nitro-benzoic acid methyl ester (Denny et al.: J. Med. Chem, 1990, 43, 814) (500 mg, 2.54 mmol) in ethanol (25 ml) was added 10% palladium on charcoal (100 mg). The mixture was stirred under hydrogen atmosphere for 48 h. The catalyst was filtered and the filtrate was evaporated to afford the product (316 mg, 75%). $^1$H NMR (300 MHz, CDCl$_3$) 7.47 (1H, dd), 6.85 (1H, dd), 6.60 (1H, t), 4.50 (4H, br s), 3.87 (3H, s).

Step b. 2-[5-(Adamantan-1-yloxymethyl)-1-benzyl-2-cyclohexyl-1H-imidazole-4-yl]-1H-benzoimidazole-4-carboxylic acid methyl ester. To a solution of 5-(adamantan-1-yloxymethyl)-1-benzyl-2-cyclohexyl -1H-imidazole-4-carbaldehyde (Example 1, step f) (430 mg, 1.00 mmol) in ethanol (5 ml) was added 2,3-diamino-benzoic acid methyl ester (316 mg, 1.90 mmol). The mixture was heated at reflux for 2 h. The solvent was evaporated, the residue was dissolved in nitrobenzene (5 ml) and placed in an oil bath at 150° C. for 1 h. The solution was cooled to ambient temperature and purified by flash column chromatography (silica, DCM/ethyl acetate 9:1 to 8:2) to afford a colourless foam (184 mg, 31%). $^1$H NMR (300 MHz, CDCl$_3$) 10.92 (1H, s), 7.93 (1H, d), 7.86 (1H, m), 7.30 (4H, m), 7.06 (2H, m), 5.36 (2H, s), 5.08 (2H, 2s), 4.03 (3H, s), 2.56 (1H, m), 2.12 (3H, br s), 1.80–1.54 (19H, m), 1.29 (3H, m).

Step c. 2-[5-(Adamantan-1-yloxymethyl)-2-cyclohexyl-1H-imidazole-4-yl]-1H-benzoimidazole-4-carboxylic acid methyl ester. The product of step b (180 mg, 0.31 mmol) was hydrogenolysed using essentially the same procedure as in Example 1, step i to afford an off-white solid (138 mg, 91%). $^1$H NMR (300 MHz, CDCl$_3$) 12.33 (1H, br s), 11.25 (1H, br s), 7.91 (2H, d), 7.31 (1H, t), 4.94 (2H, br s), 4.03 (3H, s), 2.79 (1H, m), 2.20–1.30 (25H, m).

Step d. The product of step c (131 mg, 0.27 mmol) was deprotected using essentially the same procedure as in Example 3, step c to afford off-white solid (98 mg, 77%). $^1$H NMR (300 MHz, d$_6$-DMSO) 7.76 (2H, m), 7.27 (1H, s), 4.89 (2H, br s), 2.74 (1H, m), 2.10 (3H, br s), 1.95–1.58 (19H, m), 1.40–1.21 (3H, m). The acid was converted to the N-methyl-D-glucamine salt and lyophilised from water/dioxan. Found: C, 57.25, H, 7.90, N, 9.83%; C$_{35}$H$_{51}$N$_5$O$_8$.3.4H$_2$O requires: C, 57.50, H, 7.97, N, 9.58%.

EXAMPLE 5

{2-[5-(Adamantan-1-yloxymethyl)-2-cyclohexyl-1H-imidazole-4-yl]-benzooxazol-5-yl}-acetic acid The title compound was prepared according to the procedure of Example 1, with the modification that (3-amino-4-hydroxy-phenyl)-acetic acid methyl ester (prepared in two steps from (4-hydroxy-3-nitro-phenyl)-acetic acid) was used in step g instead of 3-amino-4-hydroxy-benzoic acid methyl ester. $^1$H NMR (300 MHz, d$_6$-DMSO) 12.30 (2H, br s), 7.59 (2H, m), 7.21 (1H, d), 4.86 (2H, s), 3.68 (2H, s), 2.75 (1H, m), 2.11 (3H, br s), 1.92 (2H, m), 1.79–1.49 (17H, m), 1.28 (3H, m). The acid was converted to the N-methyl-D-glucamine salt and lyophilised from water/dioxan. Found: C, 58.39, H, 7.90, N, 7.61%; $C_{36}H_{52}N_4O_9 \cdot 3.1H_2O$ requires: C, 58.44, H, 7.92, N, 7.57%.

The compounds of the examples were tested for gastrin ($CCK_2$) antagonist activity in an immature rat stomach assay. The procedure was as follows:

The oesophagus of immature rats (33–50 g, ca. 21 days old) was ligated at the level of the cardiac sphincter and the duodenal sphincter was cannulated. The stomach was excised and flushed with ca. 1 ml of unbuffered physiological saline solution. The fundus was punctured and cannulated. A further 4–5 ml of unbuffered solution was flushed through the stomach to ensure the preparation was not leaking. The stomach was lowered into a jacketed organ bath containing 40 ml of buffered solution containing $3 \times 10^{-8}$ M 5-methylfurmethide, maintained at 37° and gassed vigorously with 95% $O_2$/5% $CO_2$. The stomach was continuously perfused at a rate of 1 ml min$^{-1}$ with unbuffered solution gassed with 100% $O_2$ with the perfusate passing over an internally referenced pH-electrode fixed 12 cm above the stomach.

After 120 min of stabilisation the drugs were added directly to the serosal solution in the organ bath and after a further 60 min cumulative pentagastrin dose-response curves were started. Changes in acid secretion were monitored and the curves analysed according to Black et al., *Br. J. Pharmacol.* 1985, 86, 581.

The results obtained at gastrin ($CCK_2$) receptors are set out in Table 1.

TABLE 1

| Example | Rat Stomach $pK_B$ |
|---|---|
| 1 | 5.48 ± 0.31 |
| 2 | 5.79 ± 0.15 |
| 3 | 5.47 ± 0.23 |
| 4 | 6.43 ± 0.35 |
| 5 | 5.69 ± 0.20 |

It is found that the compositions and products of the present invention comprising a compound of formula (I) and a proton pump inhibitor reduce hyperplasia, associated with administration of proton pump inhibitors. This was measured according to the following experimental protocol.

Animals and Treatment:

40 male SPF Wistar rats (200 g) were divided into 4 treatment groups and 2 strata. The treatment of the 20 rats in the second stratum started 2 weeks after the treatment of the first stratum. The design of the study was completely randomised double blind with individual blinding; all rats were placed in a separate cage. Animals had continuous access to water and food.

Animals were treated once daily during 14 days:

Gastrin test drug made up to an appropriate dose in physiologically compatible solvent.

Preparation of Tissue:

After removal of the fundus, the stomach were rinsed with phosphate buffered saline prior to fixation with 4% formalin in Millonig buffer. After 4 hours immersion in fixative solutions at room temperature, tissue was rinsed in phosphate buffered saline (PBS), dehydrated and embedded in paraffin using the Leitz paraffin embedding station (Leitz TP 1050; Germany) dehydration module and paraffin embedding module (Leitz EG 1160; Germany).

Cross sections (3 µm thick) of the oxyntic part of the stomach were made at 3 levels, each separated by a distance of 400 µm.

Immunostaining

The following indirect immunofluorescence labeling method was used:

removal of paraffin and rehydratation of the sections followed by a blocking step primary antibodies: polyclonal guinea pig anti-histidine decarboxylase, 1/2000 (from Euro-Diagnostica) and monoclonal mouse anti PCNA 1/2500 (Clone PC10 from Sigma). All antibodies were diluted in a 0.2% BSA solution. Sections were incubated overnight at 4° C. and then washed with a BSA solution.

secondary antibodies: goat anti guinea pig coupled to CY5, 1/500 (from Jackson Laboratories) and goat anti-mouse coupled to Cy3, 1/250 (from Jackson Laboratories); incubation for 4 hours at 37° C. After rinsing with BSA and PBS solutions, sections were mounted with slowfade (Molecular Probes Europe BV), and stored at 4° C.

Imaging

Fluorescence labelling was observed with an epifluorescence microscope or a Zeiss LSM510 (Carl Zeiss Jena GmbH) confocal microscope.

By using CY5- and CY3-coupled antibodies, the high autofluorescence properties of the oxyntic mucosa were circumvented when sections are illuminated by a 488 nm (FITC channel) light source. Negative controls, by omitting the primary antibodies, and an isotype control staining for PCNA showed complete absence of staining. The specific labelling of PCNA was checked using double staining with TOPRO-3® (Molecular Probes Europe BV), a nuclear stain. Only in the most luminal located epithelial cells, non-specific cytoplasmic labelling was present. In the glandular part of the mucosa, non-specific PCNA-staining was absent.

For determination of the labelling index of ECL cells, at least 80 confocal images per rat were taken from the 3 slides at the 3 different levels. The ratio of double labelled cells (HDC+PCNA) and all HDC labelled cells yielded the labelling index of ECL cells.

Proliferation activity of ECL cells in the PPI group is expected to be increased compared with sham, GRA and

| | |
|---|---|
| Control group: | 1 ml gastrin test drug vehicle + 1 ml p.o. (gavage) 0.25% Methocel (Dow Corning) |
| PPI group: | 1 ml gastrin test drug vehicle + 1 ml p.o. (gavage) 25 mg/kg Rabeprazole in 0.25% Methocel. |
| GRA group: | 1 ml gastrin test drug + 1 ml p.o. (gavage) 0.25% Methocel |
| GRA-PPI group: | 1 ml gastrin test drug + 1 ml p.o. (gavage) 25 mg/kg Rabeprazole in 0.25% Methocel. |

GRA-PPI groups (Eissele, R., Patberg, H., Koop, H., Krack, W., Lorenz, W., McKnight, A. T., and Arnold, R. Effect of gastrin receptor blockade on endrocine cells in rats during achlorhydria. *Gastroenterology*, 103, 1596–1601, 1992). Increased proliferation by PPI will be completely blocked by GRA.

The invention claimed is:

1. A compound of formula (I)

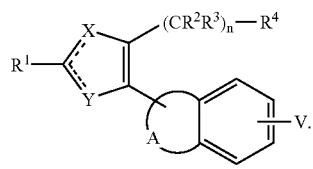

wherein

X and Y are independently selected from the group consisting of =N—; —N($R^5$)—, wherein $R^5$ is selected from the group consisting of H, Me, Et, Pr, Bn, OH and —$CH_2COOR^6$, wherein $R^6$ represents H, Me, Et, Pr or Bn); =CH; —O— and —S—;

n is from 1 to 4;

A is an optionally substituted 5-membered carbocyclic ring wherein 1 or 2 C atoms are replaced by an atom independently selected from the group consisting of N and O, A is fused with the aromatic group in formula (I) to form a fused bicycle, and (c) the ring containing X and Y is linked to a C atom of A;

$R^1$ is H or $C_1$ to $C_{15}$ hydrocarbyl wherein up to three C atoms may optionally be replaced by an atom independently selected from the group consisting of N, O, and S, and up to three H atoms may optionally be replaced by halogen atoms;

$R^2$ is selected from H, M; Et, Pr and OH, each $R^3$ being independently selected from H, Me, Et, Pr and OH when n is greater than 1;

$R^3$ is selected from the group consisting of H, Me, Et and Pr when n is 1; or, when n is greater than 1, each $R^3$ is independently selected from the group consisting of H, Me, Et and Pr, or two $R^3$ groups on neighbouring carbon atoms are linked to form a $C_3$ to $C_6$ carbocyclic ring, or two $R^3$ groups are absent from neighbouring carbon atoms which are linked by a double bond; or $R^2$ and $R^3$ on the same carbon atom together represent an =O group;

$R^4$ is $C_1$ to $C_{15}$ hydrocarbyl wherein up to two C atoms may optionally be replaced by an atom independently selected from the group consisting of N, O, and S and up to three H atoms may optionally be replaced by halogen atoms;

V is selected from the group consisting of —CO—NH—$SO_2$—Ph, —$SO_2$—NH—CO—Ph, —$CH_2OH$, and a group of the formula —$R^7U$, wherein U is selected from the group consisting of —COOH, tetrazolyl, —CONHOH— and —$SO_3H$; and $R^7$ is selected from the group consisting of a bond; $C_1$ to $C_6$ hydrocarbylene, optionally substituted by hydroxy, amino or acetamido; —C—($C_1$ to $C_3$ alkylene)-; —$SO_2NR^8$—$CHR^9$—; —CO—$NR^8$—$CHR^9$—, wherein $R^8$ and $R^9$ are independently selected from H and methyl; and —NH—(CO)$_c$—$CH_2$—, c being 0 or 1;

or a pharmaceutically acceptable salt thereof.

2. A compound according to claim 1 which is defined by formula (Ia) or (Ib)

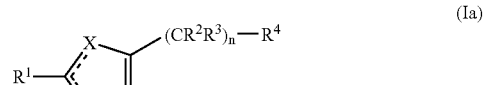

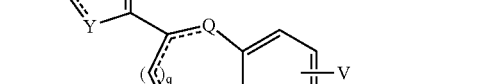

wherein

X and Y are independently selected from the group consisting of =N—; —N($R^5$)—, wherein $R^5$ is selected from the group consisting of H; Me; Et Pr Bn; OH and —$CH_2COOR^6$, wherein $R^6$ represents H, Me, Et, Pr or Bn; =CH; —O—; and —S—;

n is from 1 to 4;

$R^1$ is H or $C_1$ to $C_{15}$ hydrocarbyl wherein up to three C atoms may optionally be replaced by an atom independently selected from the group consisting of N, O, and S, and up to three H atoms may optionally be replaced by halogen atoms;

$R^2$ is selected from H, Me, Et, Pr and OH, each $R^2$ being independently selected from H, Me, Et, Pr and OH when n is greater than 1;

$R^3$ is selected from the group consisting of H, Me, Et and Pr when n is 1; or, when n is greater than 1, each $R^3$ is independently selected from the group consisting of H, Me, Et and Pr, or two R3 groups on neighbouring carbon atoms are linked to form a $C_3$ to $C_6$ carbocyclic ring, or two $R^3$ groups are absent from neighbouring carbon atoms which are linked by a double bond; or $R^2$ and $R^3$ on the same carbon atom together represent an =O group;

$R^4$ is $C_1$ to $C_{15}$ hydrocarbyl wherein up to two C atoms may optionally be replaced by an atom independently selected from the group consisting of N, O, and S and up to three H atoms may optionally be replaced by halogen atoms;

V is selected from the group consisting of —CO—NH—$SO_2$—Ph, —$SO_2$—NH—CO—Ph, —$CH_2OH$, and a group of the formula —$R^7U$, wherein U is selected from the group consisting of —COOH, tetrazolyl, —CONHOH— and —$SO_3H$; and $R^7$ is selected from the group consisting of: a bond; $C_1$ to $C_6$ hydrocarbylene, optionally substituted by hydroxy, amino or acetamido; —O—($C_1$ to $C_3$ alkylene)-; —$SO_2NR^8$—$CHR^9$—; —CO—$NR^8$—$CHR^9$—, wherein $R^8$ and $R^9$ are independently selected from H and methyl; and —NH—(CO)$_c$—$CH_2$—, c being 0 or 1;

p=0;
q=0;
Z and Q are independently =N, —NH—, =CH—, —CH$_2$—, or —O—; provided that one of Z or Q is =N—, or =CH—.

3. A compound according to claim 1 wherein the fused bicycle is derived from, benzimidazole, benzoxazole, benzofuran, isobenzofuran, indole, isoindole, indoline or isoindoline.

4. A compound according to claim 1, wherein X is =NH— and Y is —NH—, or vice versa.

5. A compound according to claim 2, wherein Q is =N; and Z is —NH or —O.

6. A compound according to claim 1, wherein $R^1$ is a substituent selected from the group consisting of $C_3$ to $C_{12}$ alicyclic; phenyl, pyridyl, phenyl $C_1$–$C_3$ alkyl and pyridyl $C_1$–$C_3$ alkyl, each group being optionally substituted with OMe, NMe$_2$, CF$_3$, Me, F, Cl, Br or I; or $R^1$ is $C_1$ to $C_8$ alkyl.

7. A compound according to claim 1, wherein $R^1$ is cyclohexyl or bicyclooctyl.

8. A compound according to claim 1, wherein V is selected from the group consisting of —CO—NH—SO$_2$—Ph, —SO$_2$—NH—CO—Ph, —OCH$_2$COOH, tetrazolyl and (CH$_2$)$_s$COOH, wherein s is from 0, 1 or 2.

9. A compound according to claim 1, wherein V is CH$_2$COOH, COOH or tetrazolyl.

10. A compound according to claim 1, wherein $R^2$ and $R^3$ are H, and n is from 1 to 3.

11. A compound according to claim 1, wherein $R^2$ and $R^3$ together form an =O group and n is 1.

12. A compound according to claim 1, wherein $R^4$ is $C_3$ to $C_{15}$ carbocyclic.

13. A compound according to claim 12 wherein $R^4$ is adamantyl, cycloheptyl, cyclohexyl or phenyl.

14. A compound according to claim 1 wherein $R^4$ is —NH—$R^{10}$ or —OR$^{10}$, in which $R^{10}$ is $C_3$ to $C_{10}$ carbocyclic.

15. A compound according to claim 14 wherein $R^{10}$ is adamantyl, cycloheptyl, cyclohexyl or phenyl.

16. A compound which is degraded in vivo to yield a compound according to claim 1.

17. A method of making a compound according to formula (Ia) wherein
p is 0
q is 0
X is —NH
Y is =N
Q is —O— or —NH
Z is =N
comprising the step of reacting a compound of formula (III), or a suitably protected derivative thereof, with a compound of formula (IV), or a suitably protected derivative thereof,

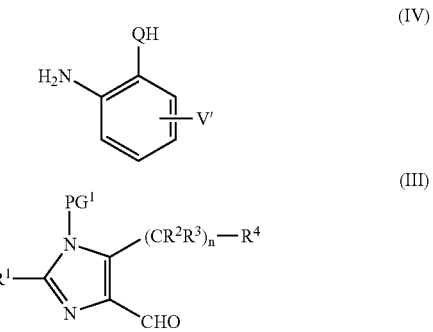

followed by heating and oxidation of the resultant imine, with concomitant cyclisation.

18. A pharmaceutical composition comprising a compound according to claim 1 together with a pharmaceutically acceptable diluent or carrier.

19. A method of making a pharmaceutical composition comprising mixing a compound according to claim 1 with a pharmaceutically acceptable diluent or carrier.

20. A method of making a pharmaceutical composition, comprising mixing a compound according to claim 1 and a proton pump inhibitor with a pharmaceutically acceptable diluent or carrier.

21. A method of treating or alleviating the symptoms of a gastrointestinal disorder, comprising administering to a patient suffering from said disorder a therapeutically beneficial amount of a compound according to claim 1.

22. The method according to claim 21, further comprising administering to said patient suffering from said disorder a therapeutically beneficial amount of a proton pump inhibitor, wherein said protein pump inhibitor and said compound are administered simultaneously, separately or sequentially.

* * * * *